United States Patent
Davenport et al.

(10) Patent No.: US 10,245,163 B2
(45) Date of Patent: Apr. 2, 2019

(54) TRIAL PROSTHESIS SYSTEM

(71) Applicant: Biomet Manufacturing, LLC, Warsaw, IN (US)

(72) Inventors: Austen Davenport, Columbia City, IN (US); Kirk J. Bailey, Rochester, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 4 days.

(21) Appl. No.: 15/325,941

(22) PCT Filed: Jul. 22, 2015

(86) PCT No.: PCT/US2015/041454
§ 371 (c)(1),
(2) Date: Jan. 12, 2017

(87) PCT Pub. No.: WO2016/014616
PCT Pub. Date: Jan. 28, 2016

(65) Prior Publication Data
US 2017/0189206 A1     Jul. 6, 2017

Related U.S. Application Data

(60) Provisional application No. 62/028,106, filed on Jul. 23, 2014.

(51) Int. Cl.
*A61F 2/46* (2006.01)
*A61F 2/36* (2006.01)
*A61F 2/30* (2006.01)

(52) U.S. Cl.
CPC .......... *A61F 2/4684* (2013.01); *A61F 2/3609* (2013.01); *A61F 2/4657* (2013.01); *A61F 2002/30617* (2013.01); *A61F 2002/365* (2013.01); *A61F 2002/3611* (2013.01); *A61F 2002/3654* (2013.01); *A61F 2002/4668* (2013.01)

(58) Field of Classification Search
CPC .. A61F 2/46; A61F 2/4684; A61F 2/36; A61F 2/3609; A61F 2/4657
See application file for complete search history.

(56) References Cited

U.S. PATENT DOCUMENTS

2011/0093087 A1    4/2011   Mcmahon et al.

FOREIGN PATENT DOCUMENTS

| DE | 102011052483 A1 | 3/2012 |
| EP | 0363019 A2 | 4/1990 |

(Continued)

OTHER PUBLICATIONS

"European Application Serial No. 15745697.1, Response filed Sep. 26, 2017 to Office Action dated Mar. 16, 2017", 15pgs.

(Continued)

*Primary Examiner* — Alvin Stewart
(74) *Attorney, Agent, or Firm* — Schwegman Lundberg & Woessner, P.A.

(57) ABSTRACT

According to various embodiments, a trial system (100) and instruments can be used to assist in confirming that a planned procedure is achieved. In various embodiments, the trial or provisional portions can include markings (110) on a trial or provisional portion to compare to one or more implanted members to ensure an planned position is achieved.

20 Claims, 2 Drawing Sheets

(56) References Cited

FOREIGN PATENT DOCUMENTS

WO    WO-2013117909 A1    8/2013
WO    WO-2016014616    1/2016

OTHER PUBLICATIONS

"International Application Serial No. PCT/US2015/041454, International Preliminary Report on Patentability dated Feb. 2, 2017", 9 pgs.

"International Application Serial No. PCT/US2015/041454, International Search Report dated Sep. 3, 2015", 6 pgs.

"International Application Serial No. PCT/US2015/041454, Written Opinion dated Sep. 3, 2015", 7 pgs.

"European Application Serial No. 15745697.1, Communication Pursuant to Article 94(3) EPC dated Apr. 16, 2018", 6 pgs.

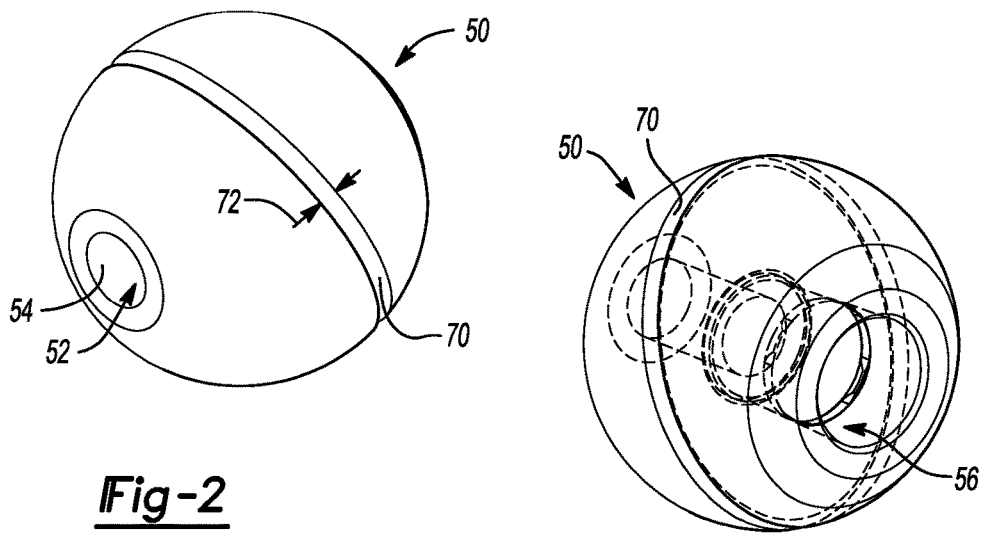
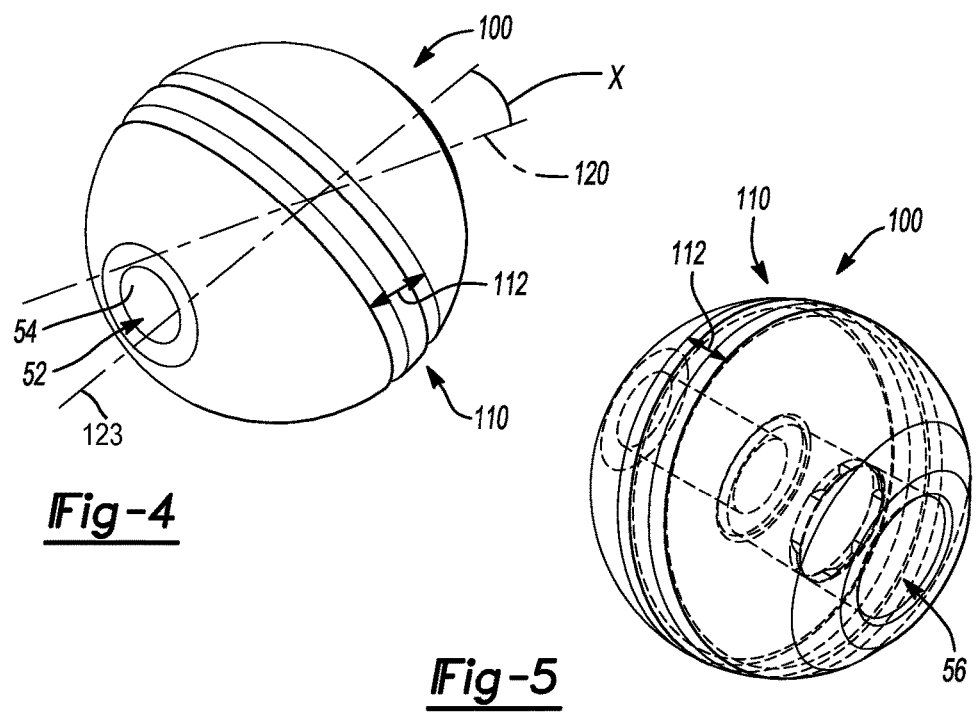

TRIAL PROSTHESIS SYSTEM

CLAIM OF PRIORITY

This application is a U.S. National Stage Filing under 35 U.S.C. 371 from International Application No. PCT/US2015/041454, filed on 22 Jul. 2015, and published as WO 2016/014616 A1 on 28 Jan. 2016, which claims the benefit of U.S. Provisional Patent Application Ser. No. 62/028,106, filed on Jul. 23, 2014, the benefit of priority of which is claimed hereby, and which is incorporated by reference herein in its entirety.

FIELD

The subject disclosure relates to a prosthesis system, and particularly to a provisional or trialing prosthesis system.

BACKGROUND

This section provides background information related to the present disclosure which is not necessarily prior art.

A procedure can be performed to position a selected member relative to another portion, such as a prosthesis in an anatomy. Using various techniques the procedure can be planned prior to performing a procedure. Planning processes can include reviewing images of a subject, measuring a subject, and experiences of an individual performing a procedure. Once planned, during a procedure, confirmation of the plan during the procedure is generally limited to a visual inspection of implanted members and/or post-procedure images acquired of the subject.

SUMMARY

This section provides a general summary of the disclosure, and is not a comprehensive disclosure of its full scope or all of its features.

In preparing for a procedure a user, such as a surgeon, can prepare or plan a procedure for a subject. The planning can include determining a size of a prosthesis, final configuration of anatomical portions, etc. The procedure can include implanting selected prosthetic components. A subject can be any appropriate subject, such as a human patient, a non-human animal patient, or a non-animal patient.

Various planning systems include the Signature™ Personalized Patient Care Systems sold by Biomet Manufacturing, LLC having a place of business in Warsaw, Ind. With for fur use with the planning system, according to various embodiments, image data can be acquired of a subject and used to plan a procedure. With the system, planning can include selecting a prosthesis and/or placement for achieving a selected outcome, such as a range of motion, bone replacement, or the like.

According to various embodiments, the planning can further include selecting a location for positioning a selected prosthesis. Selecting a prosthesis may consider a size of a naturally occurring anatomy, patient size, and other size constraints. Further, the planning can include determining an appropriate location and positioning of the prosthesis. For example, a total hip arthroplasty can include a selection of a location of an acetabular prosthesis and a femoral prosthesis. Planning may also include selecting a placement of anatomical portions after implantation, such as determining a selected final configuration. The configuration may include selecting and achieving a varus angle and/or a valgus angle. Generally, the varus and valgus angles are related to the difference between a mechanical and an anatomical axis of a long bone.

Once the planning of the procedure is completed, a procedure can be performed on a subject. In performing the procedure on a subject, confirmation of achieved goals, such as confirmation of achieving a predetermined or planned configuration of components, may be desirable. According to various embodiments, a trial system and instruments can be used to assist in assuring that a planned procedure is achieved. In various embodiments, the trial or provisional portions can include markings on the trial or provisional portion to compare to another implanted member to determine if an appropriate or planned configuration is achieved.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1. is a schematic environmental view of a Total Hip Arthroplasty System;

FIG. 2 is a perspective view of a trial femoral head, according to various embodiments;

FIG. 3 is a hollow view of the trial femoral head of FIG. 2;

FIG. 4 is a perspective view of a trial femoral head, according to various embodiments;

FIG. 5 is a hollow view of the trial femoral head of FIG. 4.

Corresponding reference numerals indicate corresponding parts throughout the several views of the drawings.

DETAILED DESCRIPTION

Figure 1:
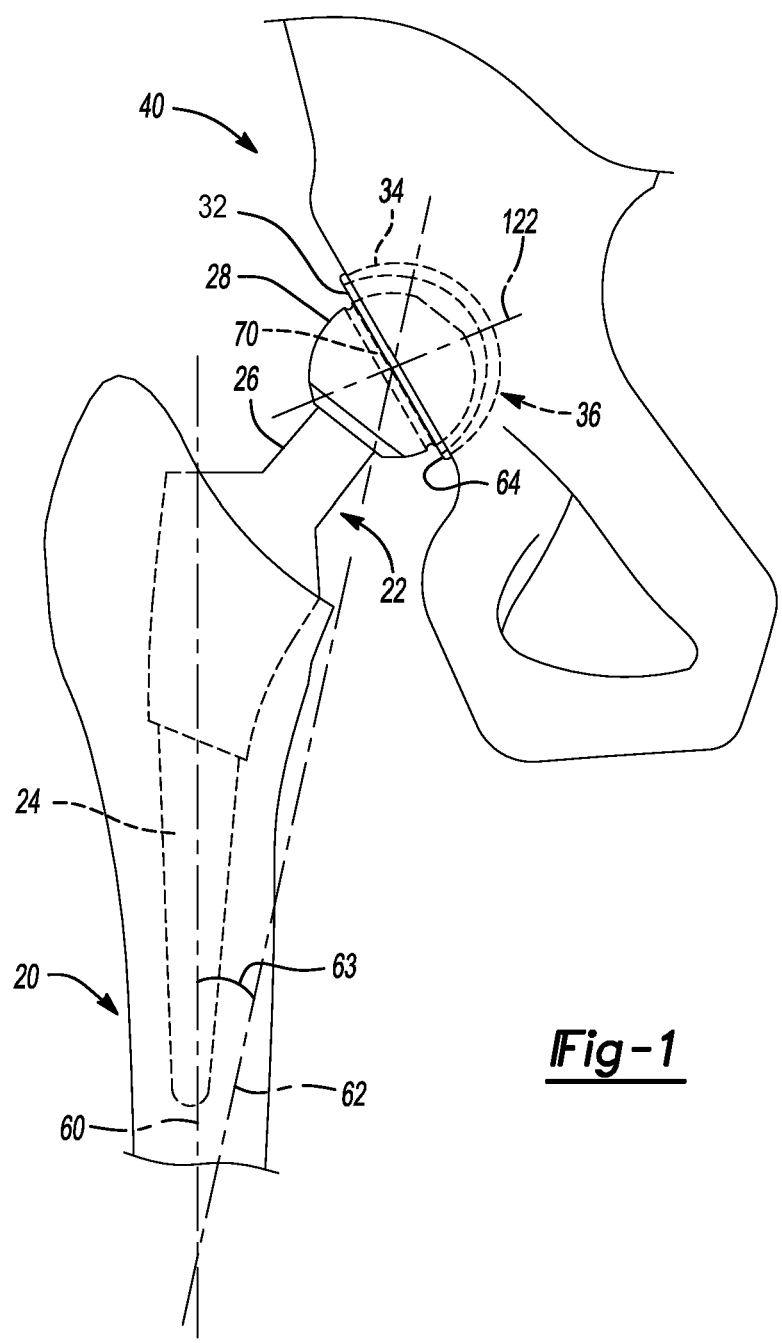

Example embodiments will now be described more fully with reference to the accompanying drawings.

According to various embodiments, a prosthesis system can include a total hip arthroplasty system that can be used in performing a total hip arthroplasty (THA). In a THA, a proximal portion of a femur is resected and replaced with an implanted prosthesis. Further, in the THA, an acetabulum is replaced with an implanted prosthesis. With reference to FIG. 1, a femur 20 can be resected and a femoral prosthesis 22 can be implanted therein. The femoral prosthesis 22 may include a stem portion 24, a neck portion 26, and a head portion 28. The stem portion 24 and the neck portion 26 may be formed as one piece or separate pieces. During implantation, the head portion 28 is generally fixedly connected to the neck portion 26. The fixed connection may be with a taper lock, locking member, or other appropriate connection appropriate for implantation.

The head portion 28, after implantation, is generally received within a bearing member 32. The head member 28 generally articulates within the bearing member 32. The bearing member 32 may, also, be received within an acetabular prosthesis 34. The acetabular prosthesis 34 may be a cup or shell that is fixed into an acetabulum 36 of a pelvis 40. The liner 32 and cup 34 may form an acetabular system.

The total hip prosthesis system including the femoral prosthesis portion 22 and the cup and bearing portions 32 and 34 can be implanted according to a plan, such as a plan determined with the Signature™ patient care system, noted above. According to various embodiments, image data can be acquired of a subject, such as a magnetic resonance image (MRI), computed tomography (CT) image, fluoroscopic image, or other image data. Image data can be evaluated or viewed in the patient planning system, such as a computer software system as noted above, for selecting or developing a plan. The patient planning system may be a computer program executed by a selected processor, such as a general purpose programmable processor and/or one or more specific processers (e.g. application specific integrated circuits). The plan can include achieving a selected varus or valgus angle, placement of femoral prosthesis, placement of a cup or bearing member 32 or 34, and other appropriate configurations. Configurations may include a final selected orientation and/or placement of bone portions relative to one another. For example, a position and orientation of a femur 20 relative to the pelvis 40. During a procedure, the stem 24 and the neck 26 can be implanted in to the femur 20 and a cup and bearing 32, 34 can be positioned within the pelvis 40 and a trial can be performed, such as to determine a selected range of motion has been achieved and/or confirming size of prosthetic components.

According to various embodiments, and with additional reference to FIGS. 2 and 3, a trial prosthetic head 50 is illustrated. The trial prosthetic head can include a connection region or section 52 such as a cylindrical or taper wall 54 that can engage the neck 26. According to various embodiments, the wall 54 can be a cylindrical wall such that it will not fixedly engage the neck 26. Thus, the trial head 50 may be temporarily placed for trialing. Accordingly, the trial head 50 can be placed on the neck 26 for a trial procedure and removed after the trial procedure and a permanent or implanted prosthesis can be positioned on the neck 26. It is understood that the femoral prosthesis can include any appropriate prosthesis system such as the Arcos® Femoral Prosthesis System, the Progressive® Total Hip System, or other appropriate hip system including those sold by Biomet Manufacturing, LLC, having a place of business in Warsaw, Ind. Selected acetabular prostheses can include the G7™ Acetabular System sold by Biomet Manufacturing, LLC. It is understood, however, that other femoral and acetabular systems can be implanted and the trial provisional head 50 can be interconnected with the selected femoral component to articulate with the selected acetabular component during a trial procedure.

The provisional head 50 can include a selected exterior dimension for achieving a plan, such as selected or determined prior to (e.g. predetermined) a procedure. The exterior dimension may be a diameter of the head. Also, placement of the connection region 52 may be selected. It is understood that the procedure can generally include portions that occur in an operating room, such as forming an incision on a subject, obtaining access to a boney portion of a subject, implanting selected prosthetic components, and the like. Pre-procedure planning can generally include acquiring image data of a subject prior to performing any invasive procedure on a subject.

The provisional femoral head 50 can be formed based upon the pre-procedure planning, such as after selecting a plan, using the Signature™ Personalized Patient Care System. As discussed above, a plan can be used to determine a size of a prosthetic member, a valgus angle, or other appropriate geometries. The valgus angle can be an angle 63 that is determined between a femoral axis 60 and a mechanical axis 62. In selecting the angle 63, a selected equator of the head 50, when implanted according to the plan, may generally be in the same plane as a rim 64 of the bearing liner 32 and/or the cup 34. The selected equator can be marked with a line, circle, or other mark or indicator 70 on the provisional head 50.

The mark 70 can be marked with a visible color, such as red, orange, or fluorescent green for easy visualization by a user. The mark 70 may also include, or alternatively, include a groove formed on the provisional head 50. Regardless, the confirmation or plan mark 70 may be formed on and/or into a surface of the head 50 based upon the planned configuration and selection of components for a prosthesis implantation procedure. With additional reference to FIG. 3, it is illustrated that the mark 70 may encircle or encompass (e.g. be annular) the head 50 such that the user can view the mark 70 at any appropriate angle relative to the other prosthetic components and anatomical portions such as the femur 20 or the pelvis 40.

In using the mark 70, the stem 24 and neck 26 can be positioned in the femur 20 and the provisional head 50 can be positioned on the neck 26. The provisional head 50 can be held in place, according to various embodiments, such as with a trial screw (not illustrated) that is passed through a trial bore 56 to engage the neck 26. The user can then move the trial head 50, now placed on the neck 26, into the bearing 32. By visualizing the mark 70 at the rim 64 of the bearing liner 32, the user can confirm that the components are implanted according to a selected plan. A user can then move the femur 20 through a range of motion relative to the pelvis 40 to ensure that a selected range of motion can be achieved. Further, the user can determine the achievement of the plan based upon an anatomical or position of the femur 20 relative to the pelvis 40.

Further, in use, the confirmation may be a visual confirmation. In other words, a user may visually view that the mark 70 is in line or in the same plane as the rim 64 of the liner 32. The user may also view the relative position of the anatomical portions during this alignment. Thus, a user may view that the selected configuration (e.g. valgus angle, varus angle, position of femur, etc.) is achieved and the placement of the mark 70 at that time. When the mark 70 is in plane with the rim 64 and the configuration of the anatomy is achieved, the user may visually determine that the prosthetic components have been placed in the anatomy in the planned positions.

According to various embodiments, the mark 70 can be a substantially single line. As a single line, such as a mark with a small width 72, the mark 70 will generally be aligned with the rim 64 of the liner 32 in only a single position or orientation of the femur 20 relative to the pelvis 40. The width 72 may be about 1 millimeter (mm) to about 3 mm. Accordingly, very precise confirmation of a selected plan can be made.

With additional reference to FIGS. 4 and 5, and continuing reference to FIG. 1, a provisional head 100 is illustrated. The provisional head 100 can be similar to the trial head 50 at least in that it can be connected with the neck 26 for trialing and/or confirming the positioning of various components of the prosthesis system. Accordingly, the trial head 100 may include the connection region 52 that includes the wall 54. As discussed above, the wall 54 of the connection region 52 can be formed as a taper, cylindrical, or other appropriate configuration to provisionally or removably interconnect with the neck 26. Further, the trial head 100 may include the passage 56 to allow for connection or passage of a screw or bolt to provisionally hold the trial head 100 in place on the neck 26.

The trial head 100, however, may include a mark region 110 that can include a dimension 112 that may be greater than a width or dimension 72 of the mark 70 on the trial head 50. The dimension 112 may be about 3 mm to about 20 mm, including about 3 mm to about 10 mm, and further including about 5 mm. In particular, the dimension 112 of the mark region 110 can be referred to or known as a confirmation region or "safe zone" for positioning the components in a patient between the femur 20 and the pelvis 40. The dimension 112 can be identified as a safe zone relating to a predetermined or planned positioning of the various components and anatomical orientation and/or configuration of the femur 20 relative to the pelvis 40. For example, when positioning the femoral head in an implanted position, the orientation of the femoral head, such as a clearance for the articulation surface relative to the liner 32, can be selected to be within a safe zone. In other words, an optimal position for the prosthetic components can be determined and a variance relative to the optimal or predetermined single location can be identified.

Accordingly, the mark 70 of the femoral head 50 can be used to identify an optimal single location of the femoral head relative to the acetabular liner 32. The safe zone marking 110, however, can identify or relate to an angular offset of the head relative to a single optimal location. For example, an axis 120 extending through the connection region 52 can be aligned with an axis 122 extending through the acetabular liner 32, as illustrated in FIG. 1. At an exact alignment, the trial head may be aligned with the rim 64 of the liner as discussed above. However, an angular offset X, such as about 1° to about 5°, illustrated by the offset axis 123 in FIG. 4, may still allow for proper articulation and range of motion of the femur 20 relative to the pelvis 40, although not in a predetermined single location. Accordingly, the rim of the liner 64 may not align within a narrow portion of the mark 70, but may be within the wider mark 110 for an entire circumference of the mark 110. Thus, the mark 110 allows for some variance from only a single selected alignment of the prosthetic components. Accordingly, when a user uses the femoral trial head 100 positioned within the acetabular liner 32, and identifies that the rim 64 is within the safe zone 110, the user can determine that the components have been properly positioned. In other words, that the plane of the rim 64 is within the bounds of the mark 110.

It is understood, however, with respect to the trial heads according to various embodiments, including the trial head 50 with mark 70 and the trial head 100 with the mark 110, that the marks 70, 110 are aligned with the rim 64 of the bearing 32 in a selected orientation and position, which may be known as a configuration. For example, the rim 64 is aligned with respective marks 70, 110 at a selected valgus angle of the femur 20 relative to the pelvis 40. Accordingly, it is understood that the trial head can be moved out of alignment with the liner 32, but that the confirmation alignment can be made when the femur 20 is in the proper or selected alignment with the pelvis 40. Further, as illustrated in the various figures, the respective marks 70, 110 can circumscribe the trial heads 50, 100, respectively. Accordingly, the user can position the femoral head on the neck 26 in any orientation and still make a determination or confirmation of a selected plan.

Further, it is understood that the trial heads 50, 100 can be substantially patient specific. Thus, the trial heads 50, 100 are designed and/or manufactured for a specific patient based upon a specific plan for that patient. Accordingly, the trial heads 50, 100 can be formed of an easily formable material such as a polymer material that can be molded or machined. Further, the marks 70, 110 can be formed during molding or formation of the trial heads 50, 100 or formed subsequently thereto. Accordingly, the trial heads can be formed as blanks, not including any of the marks, as discussed above, and the marks may be added after a plan produced by a user. The plan may be reviewed and evaluated to determine a selected orientation or optimal orientation of the femur 20 relative to the pelvis 40. This allows the marks 70, 110 to be formed substantially patient specifically. Further, it is understood that the trial heads 50, 100 can be manufactured by a supplier of the planning system or can be manufactured based upon instructions from the planning system.

Thus, the user can interconnect the trial heads 50, 100 with the neck 26, positioned within the femur 20, for confirming that the implanted configuration matches or within a selected variance of a planned configuration. The plan that was determined based upon prior or pre-procedure information, such as imaging information. As noted above the rim 64 may define a plane, or at least a portion of the rim 64 may define a plane, that may align with the marks 70, 110. The plane may intersect the marks 70, 110 when the pre-planned configuration is achieved.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A system for confirming a selected configuration of a first portion and a second portion of a prosthesis system, comprising:
   a trial femoral head member having an external surface configured to be at least partially received within an acetabular component;
   a patient-specific indicator viewable by a user on an exterior surface of the trial femoral head member; and
   a connection region configured to provisionally connect to a portion of a femoral member;
   wherein the patient-specific indicator comprises:
      a circular line indicating when a preferred single selected configuration of the femoral stem relative to the acetabular system is achieved; and a mark region disposed on either side of the circular line indicating when configurations of the femoral stem relative to the acetabular system are within a safe zone;

wherein widths of the circular line and the mark region are selected based on pre-procedure planning for a specific patient.

2. The system of claim 1, the femoral member comprising: a femoral stem configured to be implanted into a femur and interconnect with the trial femoral head.

3. The system of claim 1, further comprising:
an acetabular system including the acetabular component configured to be implanted into an acetabulum.

4. The system of claim 3, wherein the patient-specific indicator illustrates a range of configurations relative to at least the single selected configuration of the femoral stem relative to the acetabular system.

5. The system of claim 4, wherein the patient-specific indicator has a width of greater than about 3 mm.

6. The system of claim 4, wherein the patient-specific indicator includes a width to indicate an angular variation of about 1 degree to about 5 degrees from the selected single planned configuration of the femur and the pelvis.

7. The system of claim 3, wherein the patient-specific indicator is configured to be viewed relative to a rim of the acetabular system to indicate whether a predetermined configuration of the femur and the pelvis has been achieved.

8. A system for confirming a selected configuration of a first portion and a second portion of a prosthesis system, comprising:
a femoral prosthesis including a stem portion and a femoral neck portion configured to be interconnected with a femur;
an acetabular component having an articulating surface; and
a trial femoral head member having an external surface configured to provisionally engage with the articulating surface, wherein the trial femoral head includes:
an annular patient-specific indicator formed on an exterior surface of the trial femoral head member configured to be viewed relative to the acetabular component when the trial femoral head is provisionally engaging the acetabular component, wherein the annular patient-specific indicator provides an indication of a varus/valgus angle between the stem portion and the trial femoral head;
wherein the annular patient-specific indicator is selected based on pre-procedure planning for a specific patient.

9. The system of claim 8, wherein the trial femoral head further includes a bore formed in the trial femoral head to provisionally connect the trial femoral head to the femoral neck.

10. The system of claim 8, further comprising:
an acetabular shell configured to be implanted into an acetabulum;
wherein the acetabular component is fixed to the acetabular shell.

11. The system of claim 8, wherein the acetabular component has a rim and the annular patient-specific indicator is configured to be aligned with the rim at a selected configuration of the trial femoral head relative to the acetabular component for the varus/valgus angle.

12. The system of claim 8, wherein the acetabular component has a rim that defines a plane, wherein the plane intersects the annular patient-specific indicator within a selected range of angular orientations of the femoral neck relative to the acetabular component for the varus/valgus angle.

13. A method for confirming a selected configuration of a first portion and a second portion of a prosthesis system, comprising:
obtaining a blank of a trial femoral head;
evaluating a selected final configuration of a femur and a pelvis from pre-procedure data for a specific patient; and
forming a patient-specific indicator on an exterior surface of the blank to align with a rim of an acetabular component when the selected final configuration of the femur and the pelvis is achieved based on the pre-procedure data for the specific patient;
wherein the alignment of the patient-specific indicator with the rim confirms that the selected final configuration of the femur and the pelvis is achieved.

14. The method of claim 13, further comprising:
evaluating the pre-procedure data for the specific patient to determine the selected final configuration of the femur and the pelvis; and
determining a location on the exterior surface to form the patient-specific indicator to indicate the determined selected final configuration of the femur and the pelvis.

15. The method of claim 14, further comprising:
forming the blank of the trial femoral head for the specific patient before obtaining the pre-procedure data for the specific patient and forming the patient-specific indicator on the blank at the determined location after evaluating the selected final configuration of the femur and the pelvis from the pre-procedure data for the specific patient.

16. The method of claim 15, wherein the pre-procedure data for the specific patient includes image data of the specific patient.

17. The method of claim 15, wherein the patient-specific indicator is formed to identify a single configuration of the femur and the pelvis.

18. The method of claim 15, wherein the patient-specific indicator is formed to identify a safe zone of positions of the femur relative to the pelvis relative to a single configuration of the femur and the pelvis.

19. The method of claim 13, further comprising: forming the patient-specific indicator to be an annular mark on the exterior surface.

20. The system of claim 8, wherein the annular patient-specific indicator comprises:
a circular line indicating when a preferred single selected configuration of the stem portion relative to the acetabular component is achieved for the varus/valgus angle; and
a mark region disposed on either side of the circular line indicating when configurations of the stem portion relative to the acetabular component are within a safe zone;
wherein widths of the circular line and the mark region are selected based on the pre-procedure planning for the specific patient.

* * * * *

UNITED STATES PATENT AND TRADEMARK OFFICE
CERTIFICATE OF CORRECTION

PATENT NO. : 10,245,163 B2
APPLICATION NO. : 15/325941
DATED : April 2, 2019
INVENTOR(S) : Davenport et al.

Page 1 of 1

It is certified that error appears in the above-identified patent and that said Letters Patent is hereby corrected as shown below:

In the Claims

In Column 8, Line 57, in Claim 20, delete "stern" and insert --stem-- therefor

Signed and Sealed this
Twenty-first Day of April, 2020

Andrei Iancu
*Director of the United States Patent and Trademark Office*